United States Patent [19]
Castillenti

[11] Patent Number: 5,147,316
[45] Date of Patent: Sep. 15, 1992

[54] LAPAROSCOPIC TROCAR WITH SELF-LOCKING PORT SLEEVE

[76] Inventor: Thomas A. Castillenti, P.O. Box 8728, Warren, Ohio 44484

[21] Appl. No.: 615,394

[22] Filed: Nov. 19, 1990

[51] Int. Cl.⁵ .............................................. A61B 17/34
[52] U.S. Cl. .................. 604/164; 604/174; 606/185
[58] Field of Search ............ 604/174, 164, 169, 170, 604/165, 166, 42, 167, 168, 264; 606/192, 185

[56] References Cited

U.S. PATENT DOCUMENTS

| | | | |
|---|---|---|---|
| 2,687,131 | 8/1954 | Raiche | 128/349 |
| 2,936,760 | 5/1960 | Gants | 128/349 |
| 3,046,988 | 7/1962 | Moreau et al. | 128/325 |
| 3,459,175 | 8/1969 | Miller | 604/174 X |
| 3,817,251 | 6/1974 | Hasson | 128/348 |
| 4,112,932 | 9/1978 | Chiulli | 128/3 |
| 4,318,401 | 3/1982 | Zimmerman | 128/214 |
| 4,664,114 | 5/1987 | Ghodsian | 128/344 |
| 5,002,557 | 3/1991 | Hasson | 604/174 X |

Primary Examiner—Michael H. Thaler
Attorney, Agent, or Firm—Webb, Burden, Ziesenheim & Webb

[57] ABSTRACT

A laparoscopic trocar has a sleeve which may be selectively fixed to an abdominal wall by a bumper in cooperation with a balloon mounted on the distal end of the sleeve. After the trocar and the distal end of the sleeve are inserted into the abdomen, the trocar is withdrawn from the sleeve and the balloon is inflated by a syringe through the distensible coupling and a balloon inflation duct. The sleeve includes ratchets on its outer surface, and the bumper has a ratchet tooth in its inner channel. The bumper is free to slide over the ratchets in the direction of the balloon in order to clamp the abdominal wall between the bumper and the balloon. The ratchet tooth ensures that the bumper will not move backward along the sleeve, and a hands-free conduit for insertion of surgical instruments into the abdominal cavity is thereby created. The bumper may be released and the balloon deflated to permit removal of the sleeve from the abdomen.

4 Claims, 5 Drawing Sheets

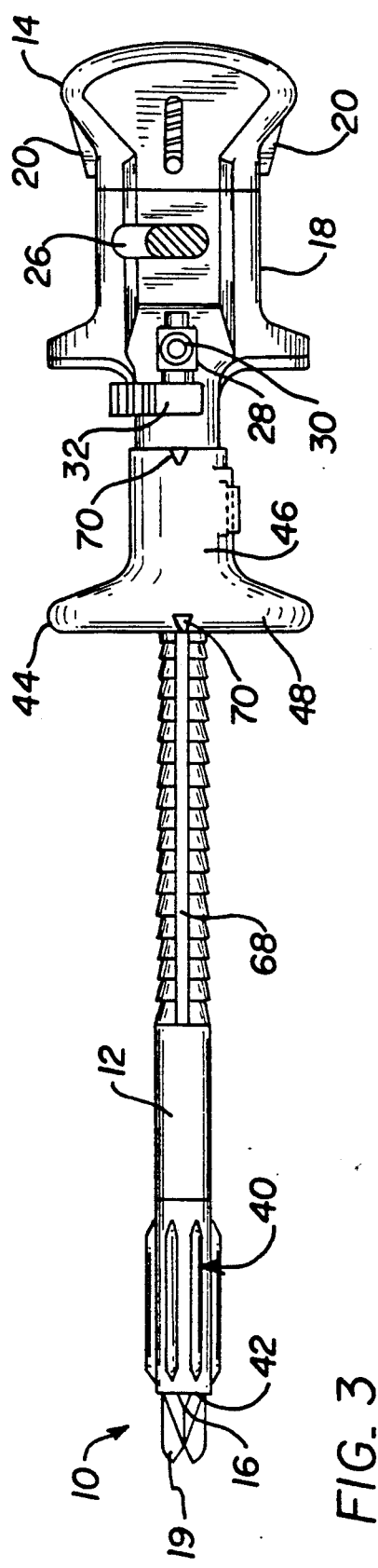
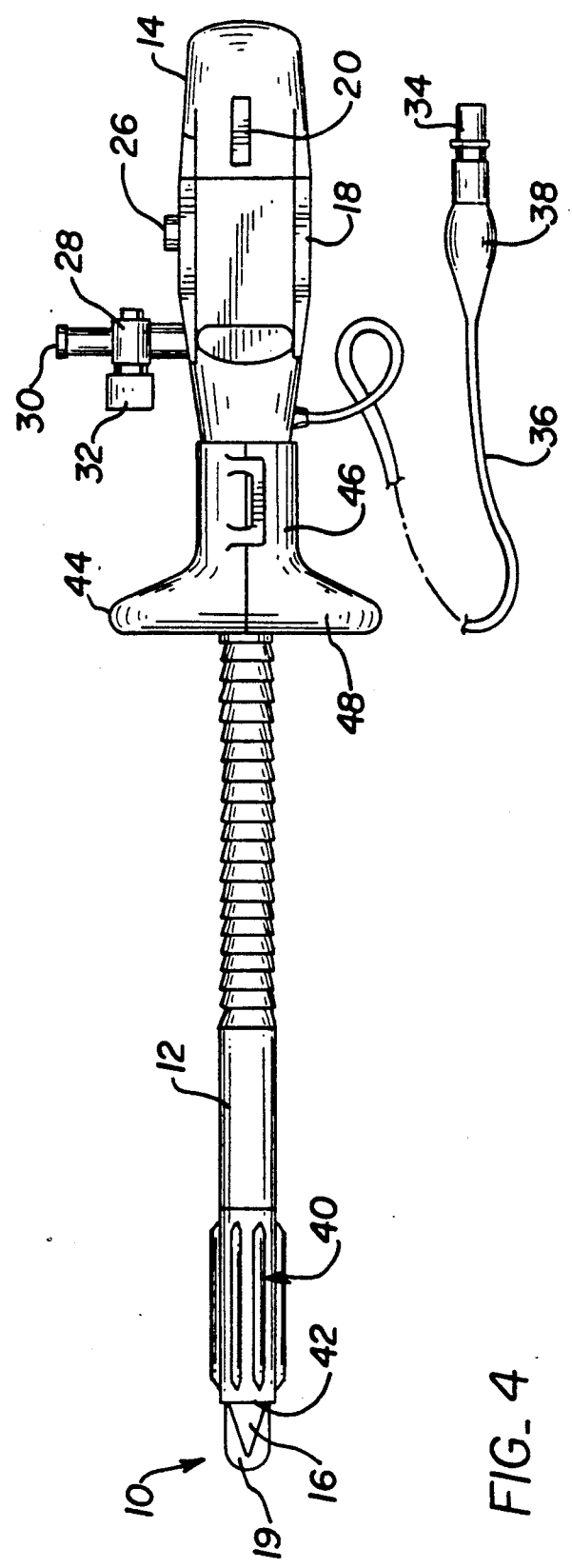

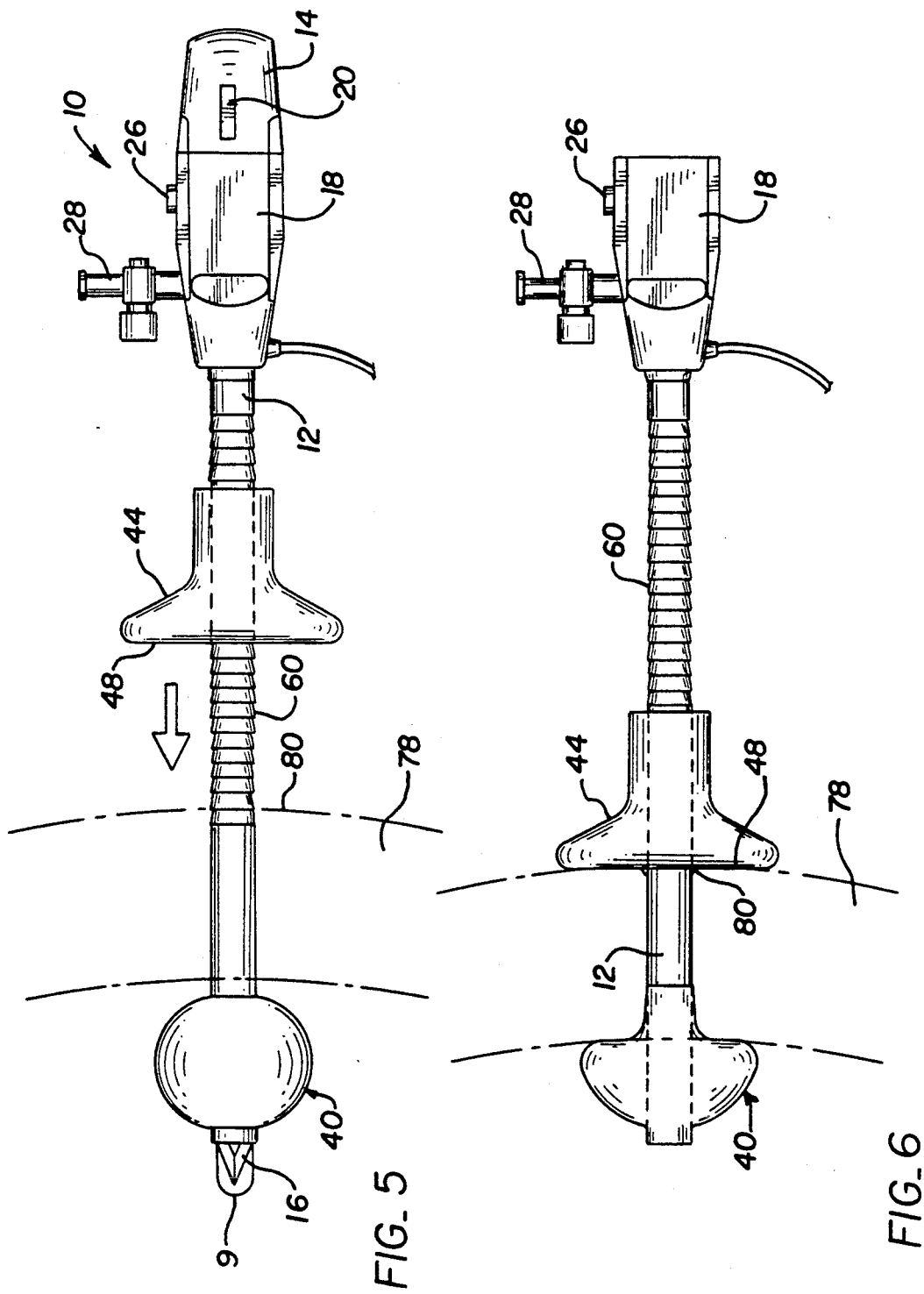

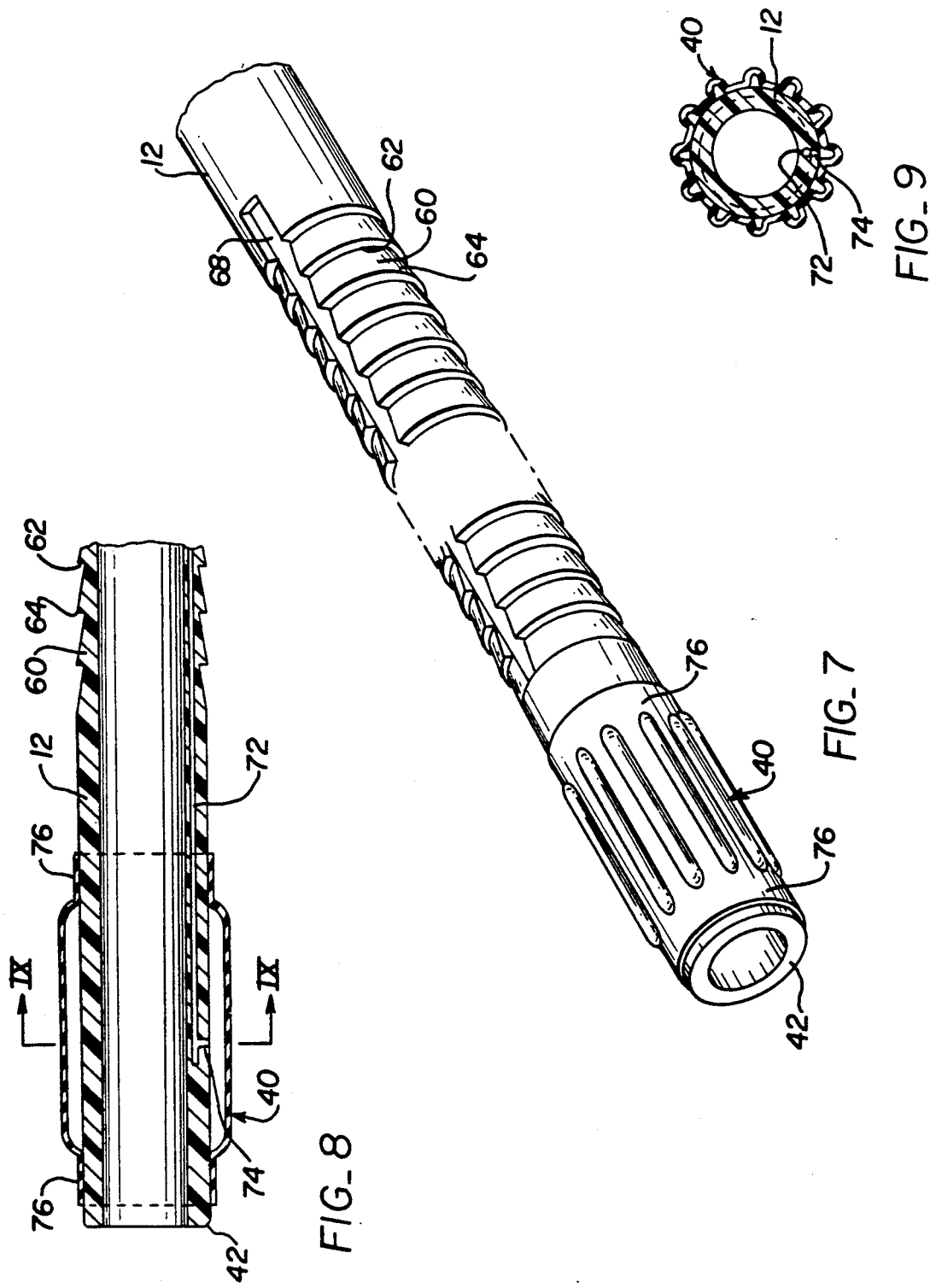

LAPAROSCOPIC TROCAR WITH SELF-LOCKING PORT SLEEVE

BACKGROUND OF THE INVENTION

1. Field Of The Invention

This invention relates to surgical instruments which provide a conduit to a body cavity to be treated and, more particularly, to instruments which provide a conduit for admitting gas, fiberoptic cameras and long handled surgical instruments into the abdominal cavity.

With improvements in medical technology and fiberoptics, surgical procedures requiring minimal incisions into the patient have become commonplace. In laparoscopic surgical procedures, it is now common to inflate the abdomen with gas, preferably carbon dioxide, in order to provide better vision of the organ or tissue to be treated as well as to provide more room for manipulation of the surgical instruments. As a result, surgical procedures which previously required opening of the abdomen with a large incision can now be performed through puncture holes. These improved techniques have a wide application in gynecological surgery and most recently in biliary tract, or gall bladder, surgery. When smaller incisions are used, the patient's risks of developing post-operative complications, such as bleeding, infection or hernia formation, are reduced. Additionally, shorter hospital stays are required. Good vision and maintained inflation of the abdomen are the keys to performing a successful surgical procedure in accordance with this method.

2. Description Of The Prior Art

U.S. Patent No. 3,817,251 to Hasson discloses a laparoscope cannula which includes an adjustable cone-shaped sleeve for blocking the incisional gap and maintaining the inflation of the abdominal cavity. Note that the cannula also includes a pair of hooks for receiving a suture to maintain the cannula in place with respect to the patient's abdomen.

U.S. Pat. No. 3,046,988 to Moreau et al. discloses an esophageal nasogastric tube having a nasal cuff made from plastic sponge which is slideably mounted onto the proximal end of a tube. The distal end of the tube includes a balloon which inflates inside of the stomach to hold the tube in proper position and prevent it from coming out of the stomach.

U.S. Pat. No. 2,936,760 to Gants discloses a positive pressure catheter having a balloon slideably mounted on the catheter tube at the proximal end with a relatively stationary balloon at the distal end for insertion and inflation within the bladder. The slideable balloon is then drawn tight against the patient to maintain the catheter in the desired position. U.S. Pat. No. 2,687,131 to Raiche discloses a catheter of similar design. Other well-known catheters include a balloon inflatable within the stomach and a flange which must be sutured to the skin outside the abdominal wall to hold the catheter in place.

FIGS. 1 and 2 show the instrumentation which is currently available for creating a port in the abdominal wall to admit fiberoptic cameras and long handled instruments into the abdominal cavity. A laparoscopic trocar A having a port sleeve B is inserted through the abdominal wall. The surgeon then releases the trocar A from the sleeve B by depressing a pair of spring-loaded tabs C and pulling trocar A from the sleeve B. Each tab C includes a tongue D at its downward end to secure the handle of trocar A to the handle of sleeve B.

FIG. 2 shows the trocar A after removal from the sleeve B. Trocar A includes a shaft E and a pyramid blade F, which are received by sleeve B in a telescoping manner. Trocar A also includes a safety sheath G which covers blade F and which extends the full length of shaft E. The safety sheath G is spring-loaded to retract within the handle of trocar A. Retraction of safety sheath G is controlled by a sheath trip H located on the bottom of the trocar handle. When sheath trip H is depressed, the safety sheath G is unlocked, and the sheath is then retractable.

Once the trocar A is removed from sleeve B, after insertion into the abdomen, a conduit for admitting gas and surgical instruments to the abdominal cavity is created. Sleeve B includes a flap valve I which is biased in the closed position for maintaining inflation within the abdominal cavity after gas has been pumped therein. Flap valve I may be opened for admittance of surgical instruments through sleeve B.

Two major problems exist with prior art sleeve B. First, inflation gas escapes from the abdominal cavity around the sleeve B and adjacent tissue when the sleeve is manipulated by the surgeon to move the camera and the instruments during the operation. Secondly, it is difficult to maintain the proper depth of insertion of sleeve B through the abdominal wall, resulting in inadvertent withdrawal of sleeve B from the puncture incision. This delays the operation because the sleeve must be reinserted in the puncture and additional inflation gas must be admitted into the abdomen. To prevent such problems, the surgeon must keep one of his hands on sleeve B to maintain the sleeve in the proper position. This hand could be more efficiently used in steering the operating instruments.

It is, therefore, an object of the present invention to provide a trocar with a sleeve that may be fixed on the abdominal wall without the need to hold the sleeve in place. It is a further object to provide an air-tight seal around the puncture incision so that inflation of the abdominal cavity is maintained for optimal visibility and easier instrument manipulation.

SUMMARY OF THE INVENTION

A surgical trocar having a trocar handle which carries a shaft and a blade is provided. The trocar is received by a sleeve which is fixable in an incision. The sleeve is carried on a sleeve handle having a bore which is concentric with the sleeve for receiving the shaft. A balloon is located at an end of the sleeve which is opposite the sleeve handle, and the balloon is inflatable to form an enlarged, annular region around the end of the sleeve. Means for inflating and deflating the balloon are included.

A bumper is slideably mounted on the sleeve between the balloon and the sleeve handle. Means are included for securing the bumper at a selected location along the sleeve to clamp the tissue surrounding the incision between the balloon and the bumper. The bumper may include a first portion and a second portion which are engageable on one another to slideably encase the sleeve.

The sleeve may include ratchets along its outer surface between the sleeve handle and the balloon. The means for securing the bumper then includes at least one ratchet tooth in the bumper for engaging the ratchets.

The sleeve may further include a longitudinal groove for receiving the ratchet tooth to allow free sliding movement of the bumper in either direction along the sleeve. The means for inflating and deflating the balloon may include a balloon inflation duct, as well as a syringe and a syringe inflation port in fluid communication with the balloon inflation duct.

Further features and advantages of the present invention will become more apparent from the following detailed description in conjunction with the accompanying drawings.

BRIEF DESCRIPTION OF THE DRAWINGS

FIG. 3 is a plan view of a trocar with a self-locking sleeve in accordance with the present invention;

FIG. 4 is a side elevation view of the trocar of FIG. 3;

FIG. 5 is a schematic view of the trocar of FIG. 3 inserted in an abdominal wall;

FIG. 6 is a side elevation view of the sleeve of FIG. 3 fixed on an abdominal wall with the trocar removed;

FIG. 7 is a partial perspective view of the sleeve of FIG. 3;

FIG. 8 is a sectional view of the sleeve of FIG. 7;

FIG. 9 is a sectional view taken along lines IX—IX of FIG. 8;

DETAILED DESCRIPTION OF THE PREFERRED EMBODIMENT

Figure 1:
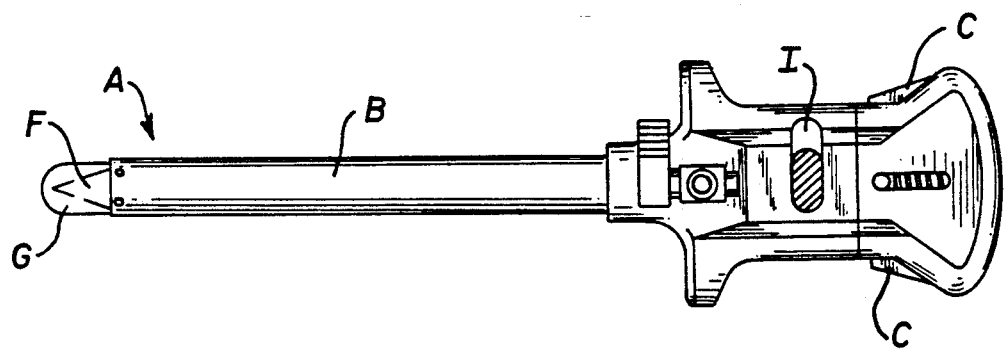
FIG. 1 is a plan view of a prior art trocar with a port sleeve.

Referring to FIGS. 3 and 4, a laparoscopic trocar 10 is shown in accordance with the present invention. The trocar 10 includes a sleeve 12, which is an elongated tube having a throughbore, into which trocar 10 is disposed. The sleeve may be fixed in an incision made in an abdominal wall as further discussed below. Trocar 10 has a trocar handle 14 at one end and a blade 16 at the opposite end. Similarly, sleeve 12 has a sleeve handle 18 at its end adjacent trocar handle 14. Trocar 10 also includes a blade 16 on a shaft as shown at E in FIG. 2. The shaft and the blade are housed in a protective sheath 19, and the sheath is retractable, as noted in the Background discussion above.

Figure 2:
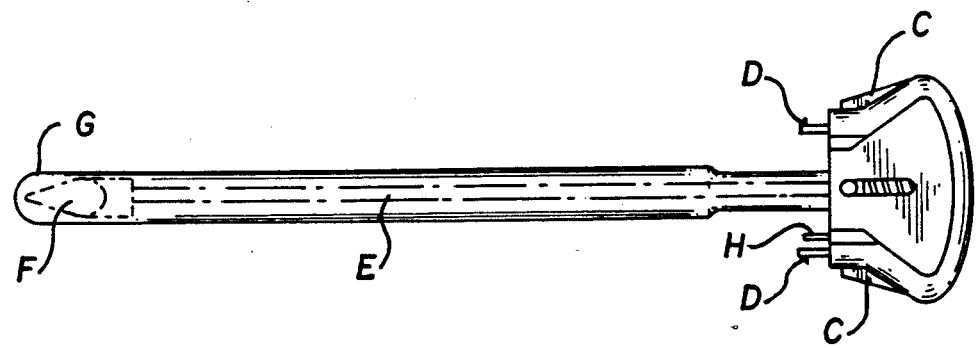
FIG. 2 is a plan view of the prior art trocar of FIG. 1 after removal from the sleeve.
Figure 13:
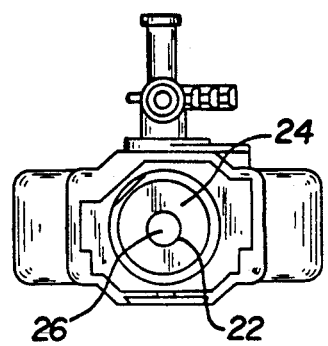
FIG. 13 is an end view of the sleeve of FIG. 6, as viewed from the right.

Trocar handle 14 has a pair of tabs 20 which are identical in structure and function to the tabs C, discussed in connection with the prior art trocar in FIGS. 1 and 2 above. Sleeve handle 18 receives trocar 10 through a bore 22, shown in FIG. 13, which is concentric with sleeve 12. Bore 22 includes a deflectable lip 24 made from elastomer material for sealing bore 22 when trocar 10 is inserted therein. Bore 22 also includes a flap valve 26 for sealing bore 22 when trocar 10 is removed. Flap valve 26 is spring biased to the closed position and is readily opened for admitting long handled instruments through sleeve 12.

Sleeve handle 18 also includes a port valve 28 for admitting gas or air into bore 22. Port valve 28 includes an inlet 30 and a stem 32 which may be rotated within a 90° angle to open and close inlet 30. A syringe port 34 is mounted to sleeve handle 18 by a length of tubing 36 with a distensible coupling bulb 38. Syringe port 34 receives a syringe (not shown) for inflation of a balloon 40 located at the distal end 42 of sleeve 12, as discussed in further detail below.

Figure 10:
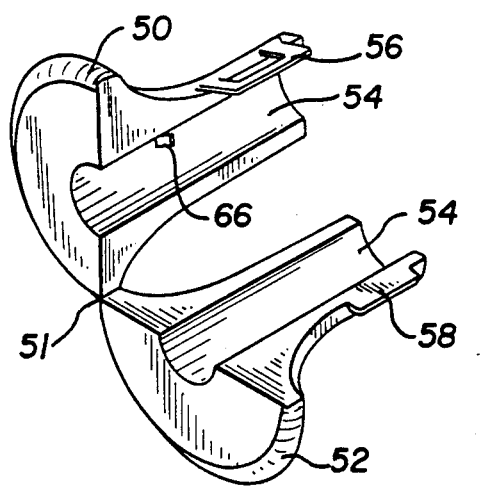
FIG. 10 is a perspective view of a bumper having a first portion and a second portion in accordance with the present invention.
Figure 11:
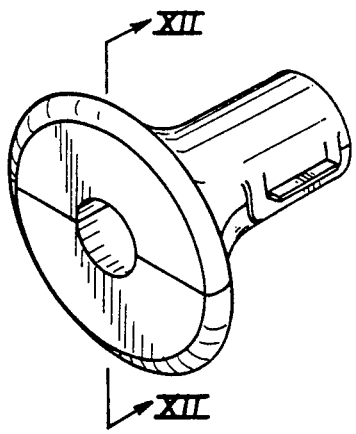
FIG. 11 is a perspective view of the bumper of FIG. 10 with the first portion and the second portion in closed engagement.
Figure 12:
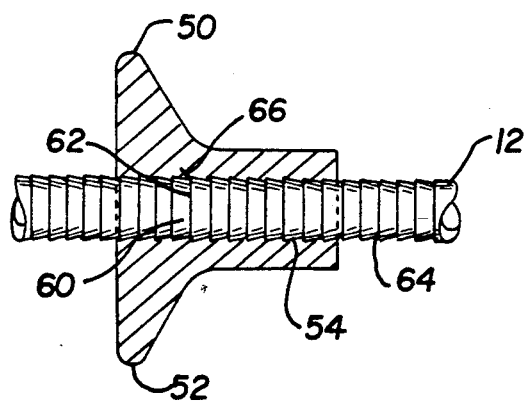
FIG. 12 is a sectional view taken along lines XII—XII of FIG. 11, with the bumper receiving the sleeve of FIG. 7.

A bumper 44 is slideably mounted on sleeve 12, and bumper 44 includes a body 46 which flares downward to a flange 48. FIGS. 3 and 4 show bumper 44 in a disengaged position, abutting sleeve handle 18. Referring to FIGS. 10-12, bumper 44 has a first portion 50 and a second portion 52 which are hingedly connected to one another as at reference 51. Each portion 50, 52 has a semicylindrical inner channel 54 so that when the first portion 50 is engaged to the second portion 52, bumper 44 encases sleeve 12 as shown in FIG. 12. First portion 50 includes a clip 56 which receives a rib 58 formed on second portion 52 to snappingly engage the two portions together. It will be understood that various closures could be substituted for the clip and rib arrangement described.

Referring to FIGS. 7 and 8, sleeve 12 includes a plurality of ratchets 60 formed in its outer surface. Each ratchet 60 includes a groove 62 and flares outward in the direction of the distal end of sleeve 12 to form a ridge 64. The ratchets 60 extend along the sleeve 12 between the sleeve handle 18 and the balloon 40. Turning to FIGS. 10 and 12, first portion 50 of bumper 44 includes a ratchet tooth 66 which is fixed in its inner channel 54. The ratchet tooth may be molded as part of first portion 50, or it may be fixed to inner channel 54 by bonding or otherwise. Ratchet tooth 66 may be metallic or plastic, and it is biased outward from inner channel 54. This bias may result from the elastic properties of the ratchet tooth, or the ratchet tooth may be spring biased. As bumper 44 is urged downward on sleeve 12, ratchet tooth 66 bends to provide clearance for ridges 64 and springs back to engage grooves 62 as shown in FIG. 12. When engaged in groove 62, ratchet tooth 66 prevents movement of bumper 44 backward in the direction of sleeve handle 18. The spring bias of ratchet tooth 66 is sufficient to keep bumper 44 in place on the sleeve 12.

Referring to FIG. 7, sleeve 12 has a longitudinal recessed groove 68 extending between sleeve handle 18 and balloon 40. This groove provides clearance for passage of ratchet tooth 66 when bumper 44, which is rotatable about sleeve 12, is positioned accordingly. To aid in aligning bumper 44, arrows 70 may be imprinted on bumper 44 as shown in FIG. 3. When a user rotates bumper 44 to align arrows 70 with recessed groove 68, bumper 44 may freely slide in both directions along sleeve 12.

As noted above, balloon 40 is fixed around sleeve 12 at distal end 42. FIGS. 3, 4 and 7 show a balloon 40 in its deflated state. Balloon 40 may be made from any suitable, distensible material as is well-known in the art. Referring to FIGS. 8 and 9, balloon 40 is put in fluid communication with tubing 36 by a balloon inflation duct 72 which is formed in the wall of sleeve 12. A shunt 74 admits the inflation air from duct 72 to balloon 40, which is fixed to sleeve 12 in an air-tight manner by a pair of seals 76.

In order to inflate balloon 40, a syringe is engaged on syringe port 34, and the syringe piston is compressed to admit air through tubing 36. Withdrawal of the syringe piston likewise draws the air from balloon 40 back up through duct 72 to deflate the balloon. It will be understood by those skilled in the art that various other arrangements for duct 72 may be equally acceptable as a conduit for inflating balloon 40.

Referring to FIGS. 5 and 6, in order to use the present invention, the trocar 10 while still housed in sleeve 12 is inserted through the abdominal wall 78. Specifically, sheath 19 is retracted on compression of the trocar 10 against the skin, and blade 16 is exposed to create a puncture incision 80 in abdominal wall 78. Sleeve 12 is then pushed through incision 80 until its distal end 42 is positioned at the desired depth within the abdominal cavity. Balloon 40 is then inflated with the syringe, and trocar handle 14 is released from sleeve handle 18 by depressing tabs 20. Trocar handle 14 is then pulled backward to remove the shaft and the blade 16 from sleeve 12.

With trocar 10 removed, sleeve 12 is then retracted a short distance so that balloon 40 engages the incision 80 as shown in FIG. 6. Bumper 44 is then urged downward along ratchets 60 until flange 48 engages the abdominal wall 78 and snugly clamps sleeve 12 thereto. Bumper 44 is automatically locked in place by ratchet tooth 66. Sleeve 12 is thus held firmly in place by cooperation of balloon 40 and bumper 44. Sleeve 12 provides a hand-free conduit for inserting long handled surgical instruments into the abdominal cavity. Further operations, including insertion of air or gas through port valve 28, may be performed without appreciable gas loss around incision 80.

If adjustment of sleeve 12 is required during the operation, bumper 44 is rotated to align arrows 70 with recessed groove 68, and bumper 44 may then be slid forward or backward on sleeve 12 accordingly. When reaching a desired position, bumper 44 is then further rotated to engage ratchet tooth 66 in the groove 62 of the adjacent ratchet 60.

After the operation is complete, flap valve 26 is opened to deflate the abdominal cavity. To remove sleeve 12 from incision 80, balloon 40 is first deflated using the suction of a syringe attached to syringe port 34, and sleeve 12 is retracted from the incision.

The present invention has applications to various surgical procedures, but it is especially applicable to gynecological surgery, as well as biliary tract, or gall bladder, surgery. Particularly, laparoscopic cholecystectomy is facilitated by use of the present invention as is operative pelviscopy, including those pelviscopic procedures which require endoscopical ligatures. The advantages realized by use of the present invention with these and other surgical procedures include the following:

1. The sleeve may be locked in position within the puncture incision by cooperation of the balloon and the bumper;
2. The amount of gas loss through the incision around the sleeve is minimized to eliminated;
3. Both of the surgeon's hands are free to conduct the surgery as one hand is not required to hold the sleeve in place within the puncture incision;
4. The sleeve will not inadvertently pop out of the puncture incision;
5. The sleeve will be automatically inserted to the proper depth within the puncture incision;
6. The invention is adaptable for use with existing trocar designs; and
7. The bumper may be adjusted so that the sleeve is custom-fitted to suit the particular thickness of the patient's abdominal wall.

Although the presently preferred embodiment of the invention has been described, is not intended to limit the invention except within the scope of the following claims.

I claim:

1. In a surgical trocar for making and inserting into an abdominal incision, said trocar having a trocar handle which carries a shaft and a blade and having a sleeve carried on a sleeve handle, said sleeve and sleeve handle having concentric bores for receiving said shaft and blade, the improvement comprising:
    a balloon at an end of said sleeve opposite said sleeve handle, said balloon inflatable to form an enlarged annular region around said end of said sleeve;
    a self-locking bumper having an inner channel slideably mounted on said sleeve between said balloon and said sleeve handle, said inner channel receiving said sleeve, wherein said bumper may be rotated with respect to the longitudinal axis of said sleeve;
    a plurality of ratchets formed in the outer surface of said sleeve between said balloon and said sleeve handle;
    at least one ratchet tooth in said inner channel of said bumper for engaging said ratchets and securing said bumper at a selected location along said sleeve to fix said sleeve in said incision by clamping an abdominal wall between said balloon and said bumper; and
    a longitudinal groove in said sleeve for receiving said ratchet tooth to allow free-sliding movement of said bumper.

2. The trocar of claim 1 wherein said bumper includes a first portion and a second portion which are engageable on one another to slideably encase said sleeve.

3. The trocar of claim 1 wherein said means for inflating and deflating said balloon includes a balloon inflation duct disposed in a wall of said sleeve, a length of tubing and a distensible coupling bulb, said coupling bulb having a port thereon for receiving a syringe.

4. The improvement of claim 1 including indicia on said bumper for locating the ratchet tooth in alignment with said longitudinal groove.

* * * * *